United States Patent
Jones et al.

(10) Patent No.: US 11,883,445 B2
(45) Date of Patent: Jan. 30, 2024

(54) LACTOCOCCUS BACTERIA AND USES THEREOF

(71) Applicant: Emory University, Atlanta, GA (US)

(72) Inventors: Rheinallt Jones, Atlanta, GA (US); Trevor Michael Darby, Atlanta, GA (US)

(73) Assignee: Emory University, Atlanta, GA (US)

( * ) Notice: Subject to any disclaimer, the term of this patent is extended or adjusted under 35 U.S.C. 154(b) by 32 days.

(21) Appl. No.: 16/980,712

(22) PCT Filed: Mar. 14, 2019

(86) PCT No.: PCT/US2019/022205
§ 371 (c)(1),
(2) Date: Sep. 14, 2020

(87) PCT Pub. No.: WO2019/178325
PCT Pub. Date: Sep. 19, 2019

(65) Prior Publication Data
US 2021/0008126 A1 Jan. 14, 2021

Related U.S. Application Data

(60) Provisional application No. 62/642,764, filed on Mar. 14, 2018.

(51) Int. Cl.
*A61K 35/744* (2015.01)
*A61K 35/747* (2015.01)
*A61K 39/09* (2006.01)
*A61K 35/00* (2006.01)
*A61K 9/00* (2006.01)
*A23L 33/00* (2016.01)

(52) U.S. Cl.
CPC ............ *A61K 35/744* (2013.01); *A23L 33/30* (2016.08); *A61K 9/0095* (2013.01); *A61K 39/09* (2013.01); *A23V 2400/231* (2023.08); *A61K 35/747* (2013.01); *A61K 2035/115* (2013.01)

(58) Field of Classification Search
None
See application file for complete search history.

(56) References Cited

U.S. PATENT DOCUMENTS

| 8,440,179 | B2 | 5/2013 | Kawakami |
| 9,049,881 | B2 | 6/2015 | Holvoet |
| 2008/0305089 | A1 | 12/2008 | Bufe |
| 2010/0021445 | A1 | 1/2010 | Kawakami |
| 2011/0002994 | A1 | 1/2011 | Beaulieu |
| 2013/0142765 | A1 | 6/2013 | Garrigues |
| 2014/0179726 | A1 | 6/2014 | Bajaj |
| 2017/0106026 | A1 | 4/2017 | Kovarik |

FOREIGN PATENT DOCUMENTS

| CA | 2677030 |   | 9/2008 |
| CN | 101616030 |   | 6/2013 |
| CN | 101616680 | A * | 6/2013 |
| EP | 1243181 |   | 9/2002 |
| EP | 2112219 |   | 5/2013 |
| WO | 2005034970 |   | 4/2005 |

OTHER PUBLICATIONS

English version of CN 101616680 A, pp. 1-22 to 21/22, 2019.*
Sethi S. Healthline Editorial Team, pp. 1-15, Nov. 11, 2021.*
Kim et al. PLOS ONE 9(6): e97841, 2014, abstract.*
Tian et al. Obesity Rev. 13: 381-387, 2012, Summary.*
Ndoye et al. J. Appl. Microbiol. 110: 499-512, 2010.*
Jeong et al. J. Korean Med. Sci. 23: 789-795, 2008.*
Culturelle, Supplement Facts, available at www.Culturelle.com, 2015.
Darby et al. Lactococcus lactis Subsp. *cremoris* Is an Efficacious Beneficial Bacterium that Limits Tissue Injury in the Intestine, iScience, 2019, 12, 356-367.
Kosaka et al., Lactococcus lactis subsp. *cremoris* FC triggers IFN-γ production from NK and T cells via IL-12 and IL-18, International Immunopharmacology, 2012, 14, 729-733.
Lee et al. Hypocholesterolemic Effect of Lactococcus lactis subsp. *lactis* biovar diacetlyactis N7 and Lactococcus lactis subsp. *lactis* 527 Strains in SD Rats, Bioscience Microflora, 2005, 24(1), 11-16.
Microbiologics (TM) Lactococcus lactis subsp. *cremoris* ATCC 19257 availabe at www.fishersci.com/shop/products.
Naudin et al. Lactococcus lactis Subspecies *cremoris* Elicits Protection Against Metabolic Changes Induced by a Western-Style Diet, Gastroenterology, 2020, 159:639-651.
Normura et al. Novel characteristic for distinguishing Lactococcus lactis subsp. *lactis* from subsp. *cremoris*, International Journal of Systematic Bacteriology, 1999, 49, 163-1 66.
Plaza et al. Modulation of immunity and inflammatory gene expression in the gut, in inflammatory diseases of the gut and in the liver by probiotics, World J Gastroenterol, 2014, 20(42): 15632-15649.

* cited by examiner

*Primary Examiner* — S. Devi

(74) *Attorney, Agent, or Firm* — Emory Patent Group

(57) ABSTRACT

This disclosure relates to methods of using beneficial bacterial such as, a *Lactococcus lactis* strain, to manage, treat, or prevent obesity, fatty liver disease, harmful ionizing radiation, and other conditions or aliments. In certain embodiments, the subject is at risk or, susceptible to, exhibiting symptoms of, or diagnosed with a disease or conditions disclosed herein. In certain embodiments, methods comprise administering an effective amount of a *Lactococcus lactis* strain to a subject in need thereof. In certain embodiments, the *Lactococcus lactis* strain is *Lactococcus lactis* subsp. *cremoris* ATCC® 19257 or a mutant thereof.

5 Claims, 7 Drawing Sheets

LACTOCOCCUS BACTERIA AND USES THEREOF

CROSS-REFERENCE TO RELATED APPLICATIONS

This application is the National Stage of International Application Number PCT/US2019/022205 filed Mar. 14, 2019, which claims the benefit of priority to U.S. Provisional Application No. 62/642,764 filed Mar. 14, 2018. The entirety of each of these applications is hereby incorporated by reference for all purposes.

BACKGROUND

Beneficial bacteria are non-pathogenic bacteria that induce an advantage to health when administered in sufficient amounts. These bacteria can prompt a change in the diversity and metabolic activity of the gut microbiota, modulate innate and adaptive immune responses, or improve epithelial barrier function. The use of beneficial bacteria to promote health is widely practiced. However, evidence corroborating the efficacy of many promoted beneficial bacteria with such claims remains limited. Lactic acid bacteria (LAB), with species from the *Lactobacillus* genus, are reported in probiotic preparations.

Overweight and obesity are increasingly common conditions in the world. Doctors measure body mass index (BMI) to screen for obesity. Obesity is a serious medical condition that can cause complications such as metabolic syndrome, diabetes, high serum cholesterol, cancers and sleep disorders. Thus, there is a need to reduce obesity.

Fatty liver, or hepatic steatosis, is a term that describes the buildup of fat in the liver. Excessive alcohol use causes fat to accumulate, damages the liver, and cirrhosis may develop. Nonalcoholic fatty liver disease (NAFLD) is a fatty liver disease associated with obesity-related disorders, such as type-2 diabetes and metabolic syndrome, occurring in people who drink little or no alcohol. Nonalcoholic steatohepatitis (NASH) is a more advanced and severe subtype of NAFLD where steatosis is complicated by liver-cell injury and inflammation, with or without fibrosis. NASH can be severe and can lead to cirrhosis, in which the liver is permanently damaged and scarred and no longer able to work properly. Insulin resistance, altered lipid storage and metabolism, accumulation of cholesterol within the liver, oxidative stress resulting in increased hepatic injury, and bacterial translocation secondary to disruption of gut microbiota have all been implicated as important co-factors contributing to progression of NASH. Due to the growing epidemic of obesity and diabetes, NASH is projected to become the most common cause of advanced liver disease and the most common indication for liver transplantation. The burden of NASH, combined with a lack of any approved therapeutic interventions, represents an unmet medical need.

Kawakami et al. report using LAB belonging to *Lactobacillus* and/or *Lactococcus* to reduce visceral fat. See U.S. Pat. No. 8,440,179.

Bufe et al. report a pharmaceutical composition having non-transgenic isolated bacteria from *Lactococcus* and *Acinetobacter* as medicament for the prevention and/or treatment of allergic or chronic inflammatory disorders. See US Patent Application Publication No. US 2008/0305089.

Kosaka et al. report that a *Lactococcus* strain, *Lactococcus lactis* subsp. *cremoris* FC, is an efficient activator of protective cellular immunity via stimulation of myeloid cells. See Int. Immunopharmacol, 2012, 14(4), 729-33.

Garrigues et al. report the use of a *Lactococcus lactis* subsp. *cremoris* strain with increased vitamin K2 production for amelioration and/or prevention of vitamin K deficiency. See US Patent Application Publication No. 2013/0142765.

Referenced cited herein are not an admission of prior art.

SUMMARY

This disclosure relates to methods of using beneficial bacterial such as, a *Lactococcus lactis* strain, to manage, treat, or prevent obesity, fatty liver disease, harmful ionizing radiation, and other conditions or aliments. In certain embodiments, the subject is at risk or, susceptible to, exhibiting symptoms of, or diagnosed with a disease or conditions disclosed herein. In certain embodiments, methods comprise administering an effective amount of a *Lactococcus lactis* strain to a subject in need thereof. In certain embodiments, the *Lactococcus lactis* strain is *Lactococcus lactis* subsp. *cremoris* ATCC® 19257 or a mutant thereof.

In another aspect, the disclosure relates to methods to control body weight or decrease the weight gain rate, comprising administrating non-pathogenic bacteria in an effective amount to a subject in need thereof, wherein the non-pathogenic bacteria comprise a *Lactococcus lactis* strain. In certain embodiments, the subject is on a high-fat Western diet prior to the administration of the non-pathogenic bacteria. In certain embodiments, the high-fat Western diet is characterized by high intakes of red and processed meat, butter, fried foods, high-fat dairy products, eggs, refined grains, potatoes, and high-sugar drinks. In certain embodiments, the high-fat Western diet has more than 35% of the calories derived from fat and more than 40% of the calories derived from carbohydrates, wherein more than 60% of the calories derived from carbohydrates are derived from sucrose. In certain embodiments, the subject is overweight, as characterized by a Body Mass Index (BMI) between 25 and 29.9. In certain embodiments, the subject has obesity, as characterized by a BMI of 30 or over. In certain embodiments, the subject has obesity-related conditions and complications, comprising stroke, and type 2 diabetes. In certain embodiments, the non-pathogenic bacteria are in the form of aqueous solution, suspension, lyophilizate, or powder. In certain embodiments, the non-pathogenic bacteria are administrated to the subject in different pharmaceutical and nutraceutical formulations, comprising beads, capsules, tablets, gels, and liquid suspensions. In certain embodiments, the non-pathogenic bacteria are administrated to the subject in the form of probiotic food and beverage products, including milk, yogurts, cheeses, creams, chocolates, meats, and other fermentation products. In certain embodiments, the *Lactococcus lactis* strain is *Lactococcus lactis* subsp. *cremoris* ATCC® 19257 or a mutant thereof.

In another aspect, the disclosure relates to methods to control or reduce the serum cholesterol level, comprising administrating non-pathogenic bacteria in an effective amount to a subject in need thereof, wherein the non-pathogenic bacteria comprise a *Lactococcus lactis* strain. In certain embodiments, the subject has a borderline high serum cholesterol level, 200-239 mg/dL. In certain embodiments, the subject has a high serum cholesterol level, >240 mg/dL. In certain embodiments, the subject is at risk of, exhibiting symptoms, or diagnosed with hypercholesterolemia. In certain embodiments, the non-pathogenic bacteria are in the form of aqueous solution, suspension, lyophilizate, or powder. In certain embodiments, the non-pathogenic bacteria are administrated to the subject in different pharmaceutical and nutraceutical formulations, comprising beads, capsules, tablets, gels, and liquid suspensions. In certain embodiments, the non-pathogenic bacteria are administrated to the subject in the form of probiotic food and beverage products, including milk, yogurts, cheeses, creams, chocolates, meats, and other fermentation products. In certain embodiments, the *Lactococcus lactis* strain is *Lactococcus lactis* subsp. *cremoris* ATCC® 19257 or a mutant thereof.

In another aspect, the disclosure relates to methods to prevent or treat hepatic steatosis, comprising administrating non-pathogenic bacteria in an effective amount to a subject in need thereof, wherein the non-pathogenic bacteria comprise a *Lactococcus lactis* strain. In certain embodiments, the subject is at risk of, exhibiting symptoms of, or diagnosed with nonalcoholic fatty liver disease (NAFLD). In certain embodiments, the subject is at risk of, exhibiting symptoms of, or diagnosed with nonalcoholic steatohepatitis (NASH). In certain embodiments, the subject is at risk of, exhibiting symptoms of, or diagnosed with alcoholic liver disease (ALD). In certain embodiments, the subject is at risk of, exhibiting symptoms of, or diagnosed with alcoholic steatohepatitis (ASH). In certain embodiments, the non-pathogenic bacteria are in the form of aqueous solution, suspension, lyophilizate, or powder. In certain embodiments, the non-pathogenic bacteria are administrated to the subject in different pharmaceutical and nutraceutical formulations, comprising beads, capsules, tablets, gels, and liquid suspensions. In certain embodiments, the non-pathogenic bacteria are administrated to the subject in the form of probiotic food and beverage products, including milk, yogurts, cheeses, creams, chocolates, meats, and other fermentation products. In certain embodiments, the *Lactococcus lactis* strain is *Lactococcus lactis cremoris* subsp. ATCC® 19257 or a mutant thereof.

In certain embodiments, disclosure relates to methods to protect against or treat symptoms caused by harmful ionizing radiation exposure, comprising administrating non-pathogenic bacteria in an effective amount to a subject in need thereof, wherein the non-pathogenic bacteria comprise a *Lactococcus lactis* strain. In certain embodiments, the harmful ionizing radiation exposure comprises X-rays, gamma rays, and particles. In certain embodiments, the radiation exposure is originated from occupational exposure, comprising healthcare facilities, research institutions, baggage scanning facilities, nuclear reactors and support facilities, nuclear weapon production facilities, mining facilities, and other manufacturing settings. In certain embodiments, the radiation exposure is originated from non-occupational exposure, comprising medical exposure, radiation fallout from nuclear weapon tests and uses, and releases from nuclear power facilities. In certain embodiments, the medical exposure is originated from medical diagnostics and therapeutics, comprising radiology and radiation therapies. In certain embodiments, the radiation therapies comprise radiation therapies for cancer. In certain embodiments, the non-pathogenic bacteria are administrated prior to the radiation exposure. In certain embodiments, the non-pathogenic bacteria are administrated after the radiation exposure and the subject may or may not develop radiation symptoms, comprising nausea and vomiting, cough, fever, fullness of the chest, shortness of breath, severe fatigue, spontaneous bleeding, bloody diarrhea, sloughing of skin, hair loss, dry mouth, mouth ulcers, difficulty swallowing, stiffness in the joints or muscles, lymphedema, tooth decay, bladder irritation, radiation fibrosis, infections, erectile dysfunction in men, lowered sperm counts or reduced sperm activity in men, changes of menstruation in women, symptoms of menopause in women, and infertility in women. In certain embodiments, the non-pathogenic bacteria are in the form of aqueous solution, suspension, lyophilizate, or powder. In certain embodiments, the non-pathogenic bacteria are administrated to the subject in different pharmaceutical and nutraceutical formulations, comprising beads, capsules, tablets, gels, and liquid suspensions. In certain embodiments, the non-pathogenic bacteria are administrated to the subject in the form of probiotic food and beverage products, including milk, yogurts, cheeses, creams, chocolates, meats, and other fermentation products. In certain embodiments, the *Lactococcus lactis* strain is *Lactococcus lactis* subsp. *cremoris* ATCC® 19257 or a mutant thereof.

In yet another aspect, the disclosure relates to methods to reduce tissue scaring, comprising administrating non-pathogenic bacteria in an effective amount to a subject in need thereof, wherein the non-pathogenic bacteria comprise a *Lactococcus lactis* strain. In certain embodiments, the tissue scaring is caused by injury, comprising traumatic laceration, burn, radiation damage, pressure necrosis, and crush injury.

In certain embodiments, the non-pathogenic bacteria are in the form of aqueous solution, suspension, lyophilizate, or powder. In certain embodiments, the non-pathogenic bacteria are administrated to the subject in different pharmaceutical and nutraceutical formulations, comprising beads, capsules, tablets, gels, and liquid suspensions. In certain embodiments, the non-pathogenic bacteria are administrated to the subject in the form of probiotic food and beverage products, including milk, yogurts, cheeses, creams, chocolates, meats, and other fermentation products. In certain embodiments, the *Lactococcus lactis* strain is *Lactococcus lactis* subsp. *cremoris* ATCC® 19257 or a mutant thereof.

In certain embodiments, this disclosure contemplates a medicament comprising *Lactococcus lactis cremoris* ATCC® 19257 or mutant thereof or probiotic formulation comprising *Lactococcus lactis cremoris* ATCC® 19257 or mutant thereof for uses disclosed herein.

In certain embodiments, this disclosure contemplates the production of a medicament comprising *Lactococcus lactis cremoris* ATCC® 19257 or mutant thereof or probiotic formulation comprising *Lactococcus lactis cremoris* ATCC® 19257 or mutant thereof for uses disclosed herein.

BRIEF DESCRIPTION OF THE DRAWINGS

FIG. 2A shows data indicating that ingestion of *Lactococcus lactis* subsp. *cremoris* ATCC® 19257 is cytoprotective against ionizing radiation insult in mice. Survival of 6-week-old C57BL/6 mice fed the indicated lactic acid bacteria daily for 3 days followed 12 Gy ionizing radiation insult was shown. Significantly enhanced survival of only mice treated before radiation for three days with *L. lactis* subsp. *cremoris* ATCC® 19257 (Log-Rank test for g-f vs. g-f+*L. lactis* subsp. *cremoris*, P<=0.0006, n=5), or with

*Lactobacillus rhamnosus* GG (Log-Rank test for g-f vs. g-f+*L. rhamnosus* GG, P<=0.0202, n=5) was observed.

Figure 2A:
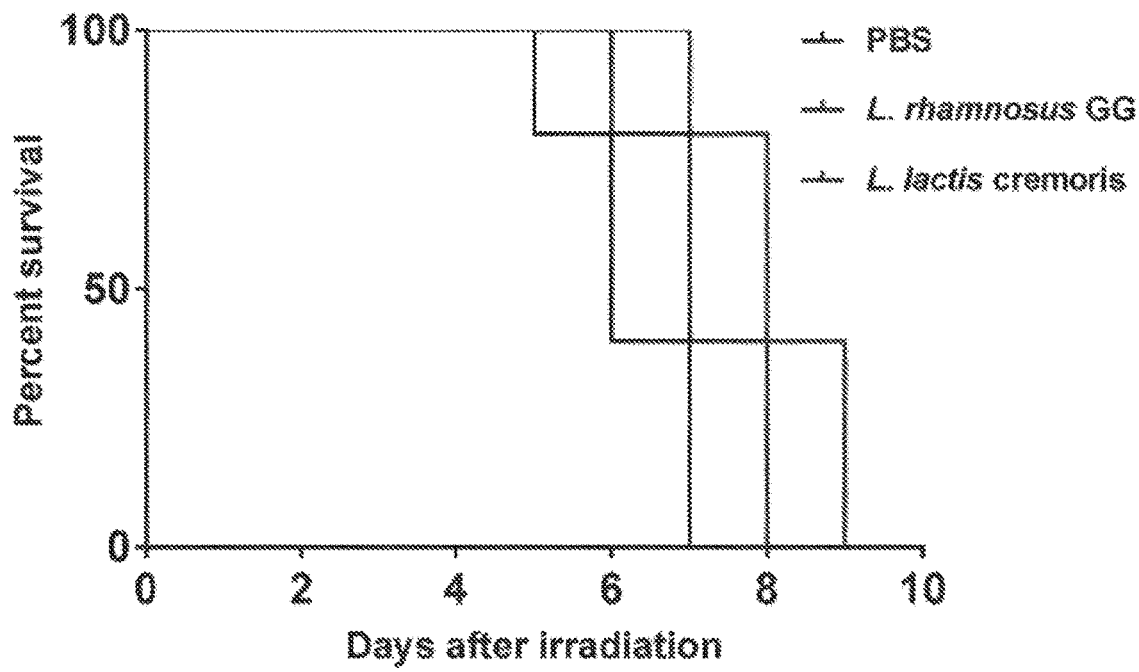
Figure 2B:
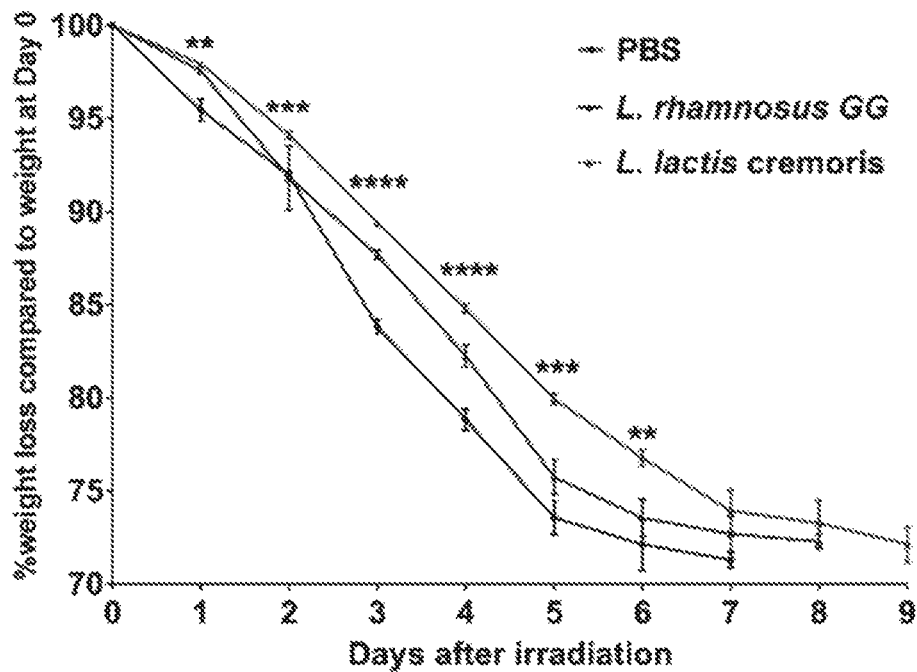

FIG. 2B shows data indicating the body weight of mice described in FIG. 2A. Mice fed either *Lactococcus lactis* subsp. *cremoris* ATCC® 19257 or *Lactobacillus rhamnosus* GG exhibited significantly enhanced preservation of body weight compared to the vehicle control.

Figure 3A:
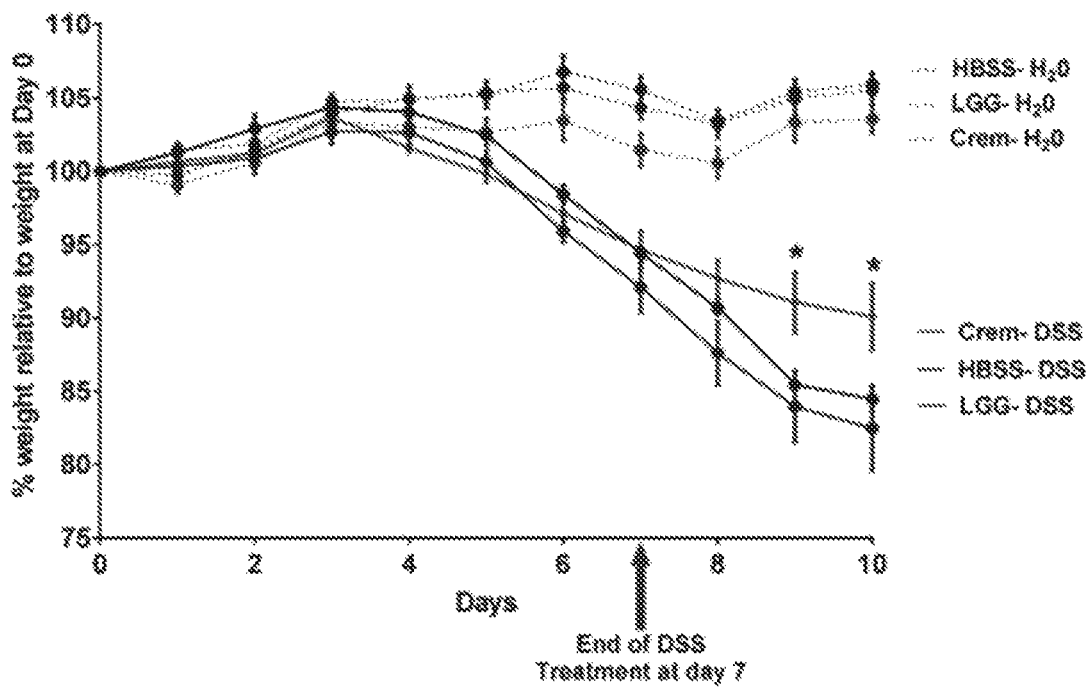

FIG. 3A shows data indicating that *Lactococcus lactis* subsp. *cremoris* ATCC® 19257 protects the murine intestine from dextran sodium sulfate (DSS)-induced colitis. Groups of ten 6-week-old C57/B6 mice were administered either $1 \times 10^8$ CFU total *Lactococcus lactis* subsp. *cremoris* ATCC 19257 (crem), or *Lactobacillus rhamnosus* GG (LGG), or vehicle control for 14 days. Feeding of bacteria was ceased before 4% DSS being included in the drinking water (day 0) for 7 days of the indicated groups. Control groups of bacteria fed mice were subjected to regular water. Measurement of weight loss in mice of the aforementioned groups following commencement of the inclusion of 4% DSS in the drinking water was performed.

Figure 3B:
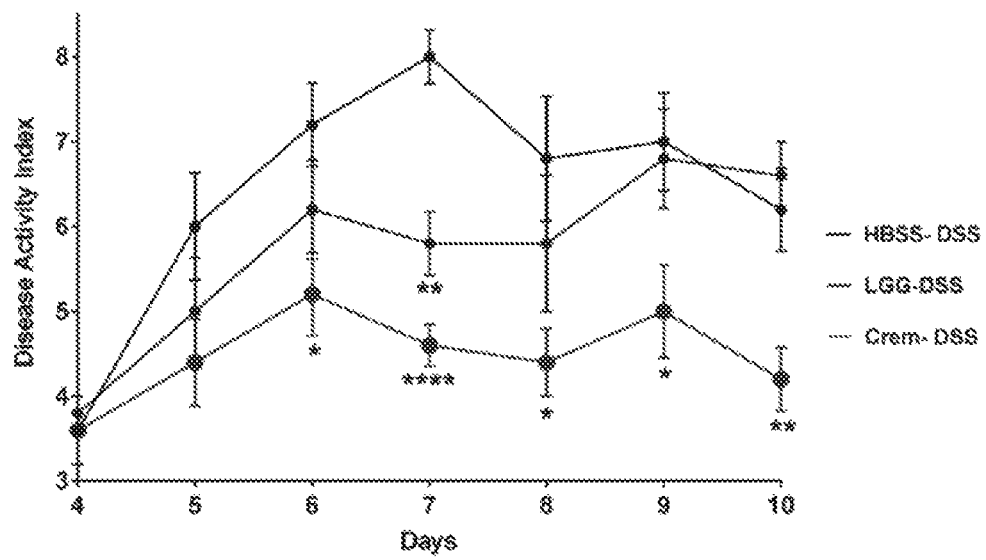

FIG. 3B shows data on the disease activity index (DAT) of mice described in FIG. 3A.

Figure 3C:
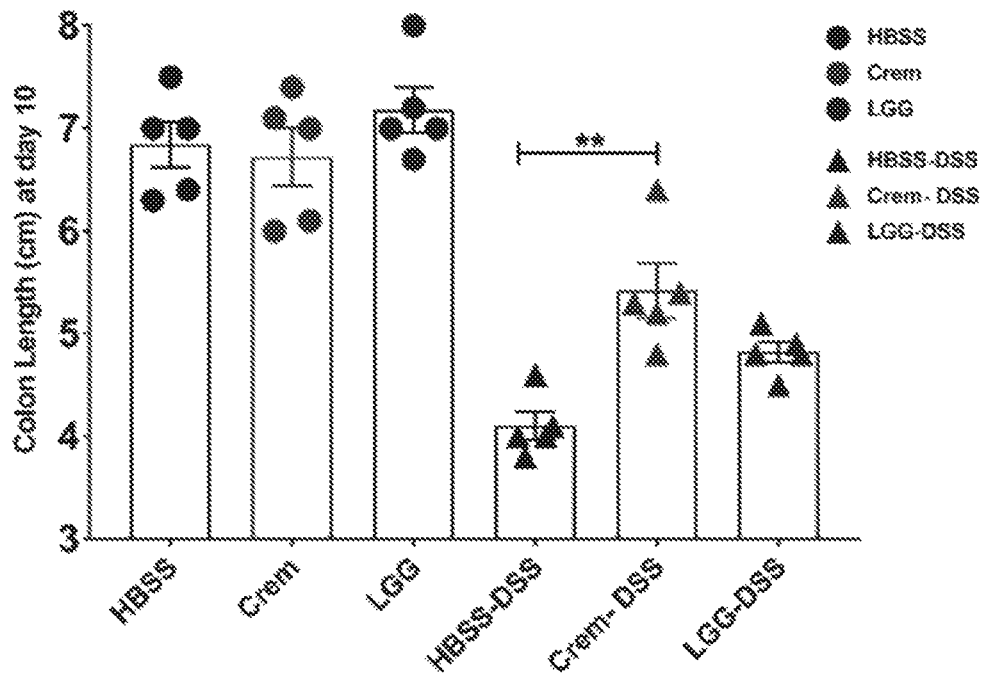

FIG. 3C shows data on the colon length of mice in FIGS. 3A and B at day 10 following commencement of treatment with DSS.

Figure 3D:
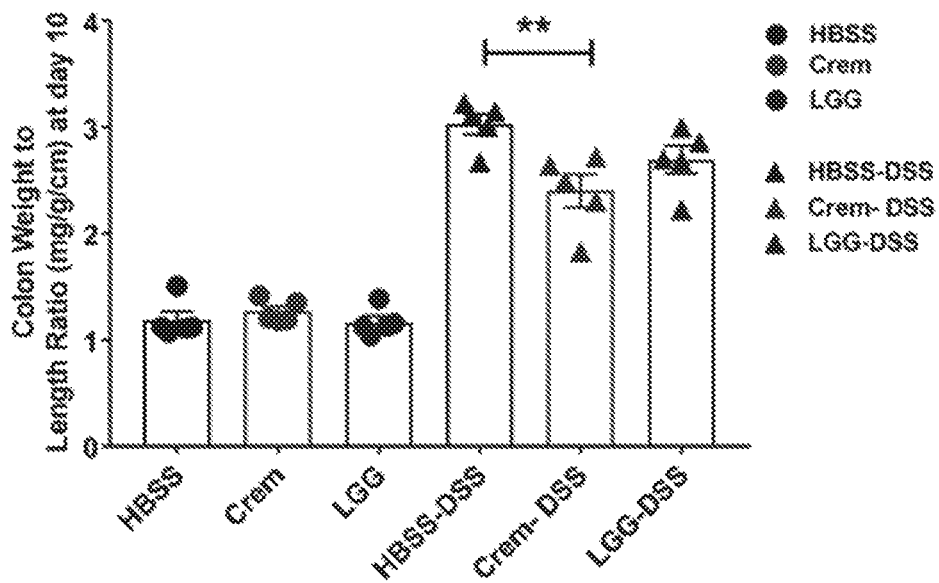

FIG. 3D shows data on the colon weight to length ratio of mice in FIGS. 3A and B at day 10 following commencement of treatment with DSS.

Figure 4:
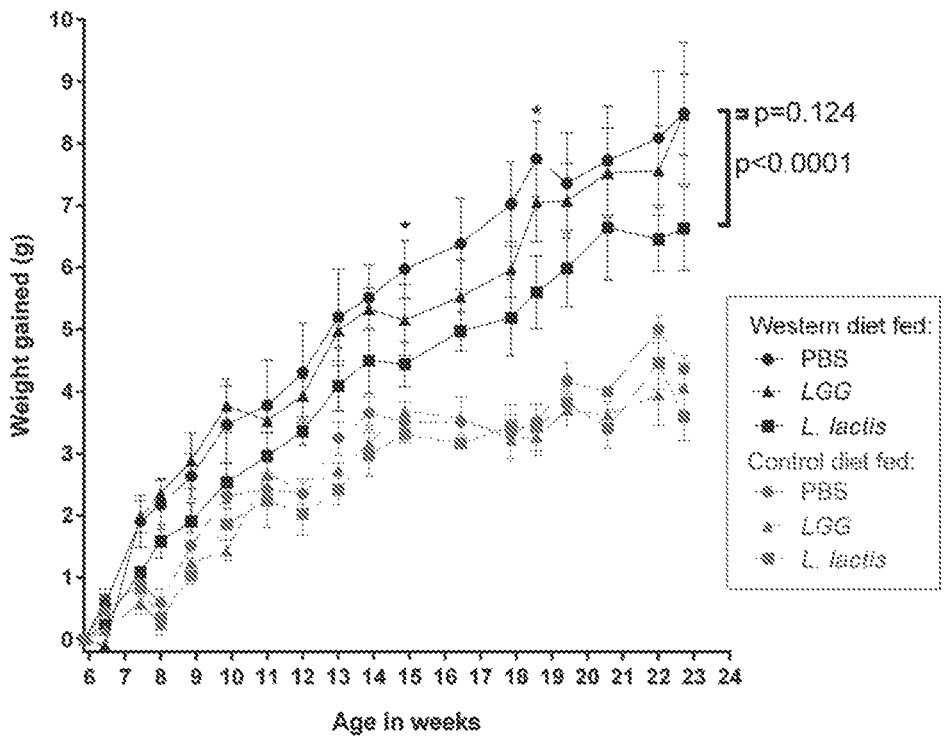

FIG. 4 shows data indicating that *Lactococcus lactis* subsp. *cremoris* ATCC® 19257 protects against Western diet-induced weight gain. Female C57BL/6 mice were administered either *L. rhamnosus* GG (LGG), *L. lactis* subsp. *cremoris* ATCC® 19257 or equal volume of PBS twice-weekly over the course of the experiment. Treatments were initiated when mice were 6-week-of-age, and the Western diet was introduced at week 7. Weights were recorded over 17 weeks (n=5). For comparison of weight gain curves, multiple linear regression was employed. Analysis of *L. lactis* subsp. *cremoris* ATCC® 19257 Western diet vs. PBS Western diet, by Student's t-test yielded a significance difference at a confidence level of P=0.0001.

Figure 5A:
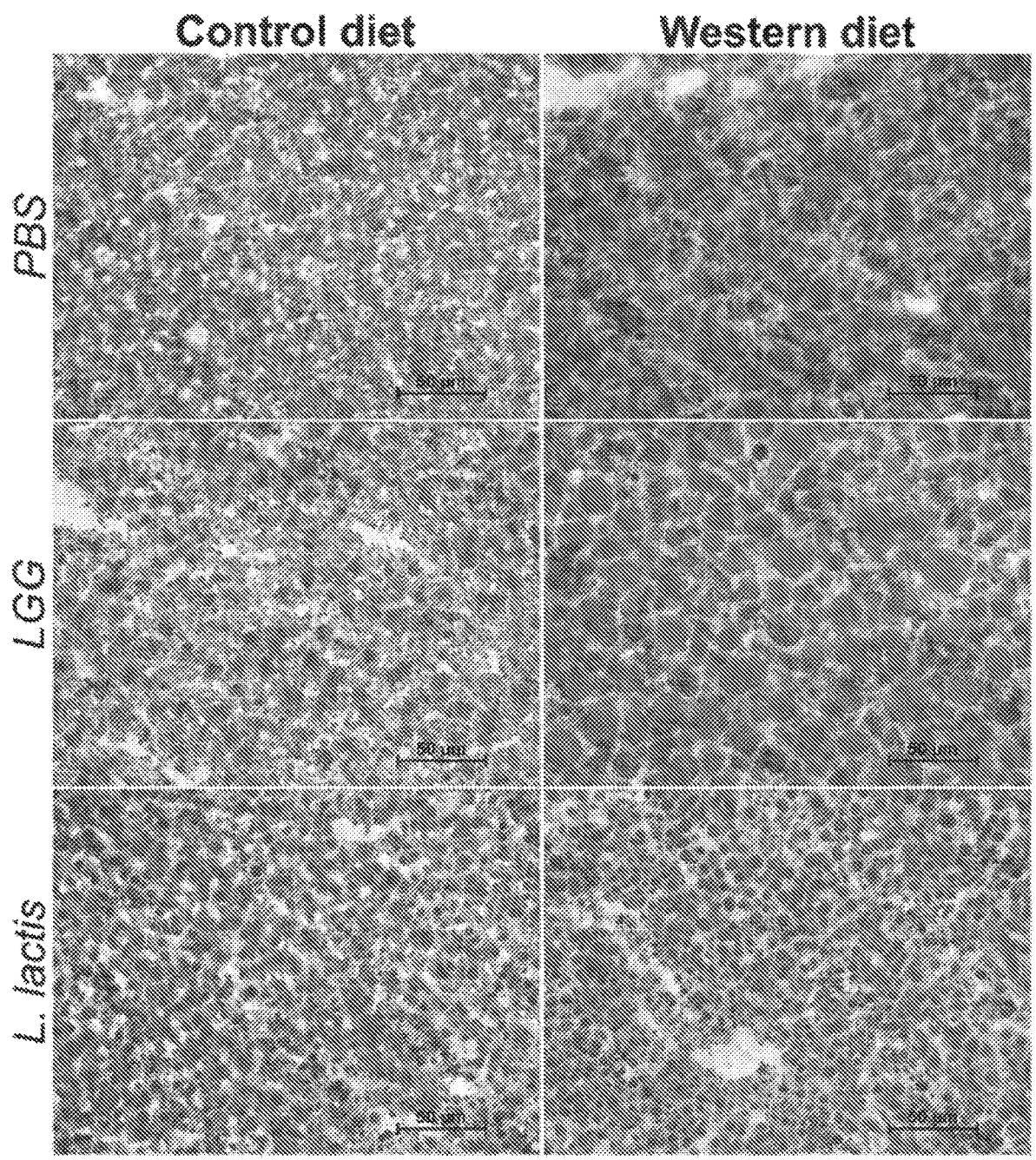

FIG. 5A shows data indicating that *Lactococcus lactis* subsp. *cremoris* ATCC® 19257 protects against Western diet-induced liver fat accumulation. Following the 17 weeks of the treatments described in FIG. 4, mice were sacrifice and histological sections of liver tissues were prepared. The histological sections were stained with Oil Red O, which is a lysochrome diazo dye used for staining of neutral triglycerides and lipids. Bars represent 50 μm.

Figure 5B:
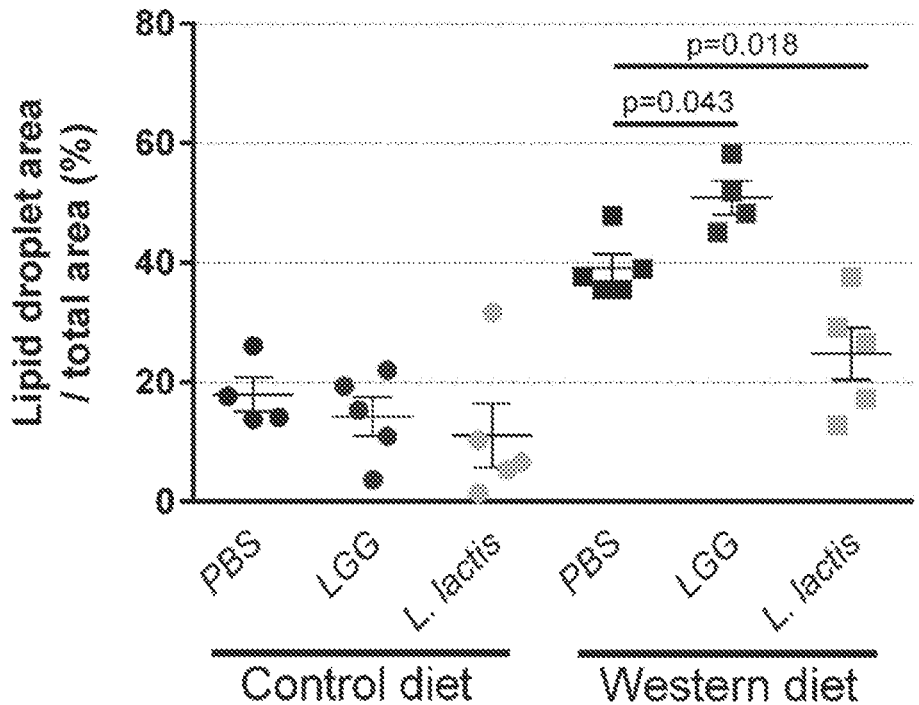

FIG. 5B shows the quantification of lipid droplet area within the liver histological sections in FIG. 5A, expressed as a percentage of total liver section area. Values were calculated using Image J analysis of 10 μm liver sections stained with Oil-red O.P-values were obtained by ANOVA followed by Tukey-Kramer post-test in comparison to the saline-treated control animals (n=4 or 5).

Figure 6:
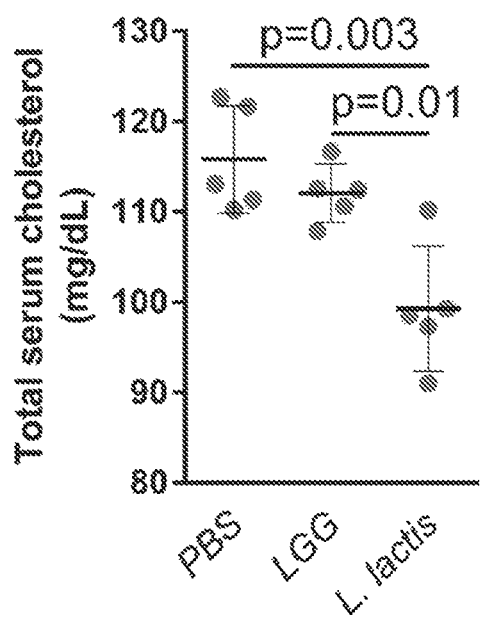

FIG. 6 shows data on the quantification of the total serum cholesterol level. At 8 weeks of bacterial treatments, serum was prepared from cheek bleeds from the experimental mice. The serum samples were assessed by enzymatic assay for total serum cholesterol amounts. P-values were obtained by ANOVA followed by Tukey-Kramer post-test in comparison to the saline-treated control animals (n=5).

Figure 7:
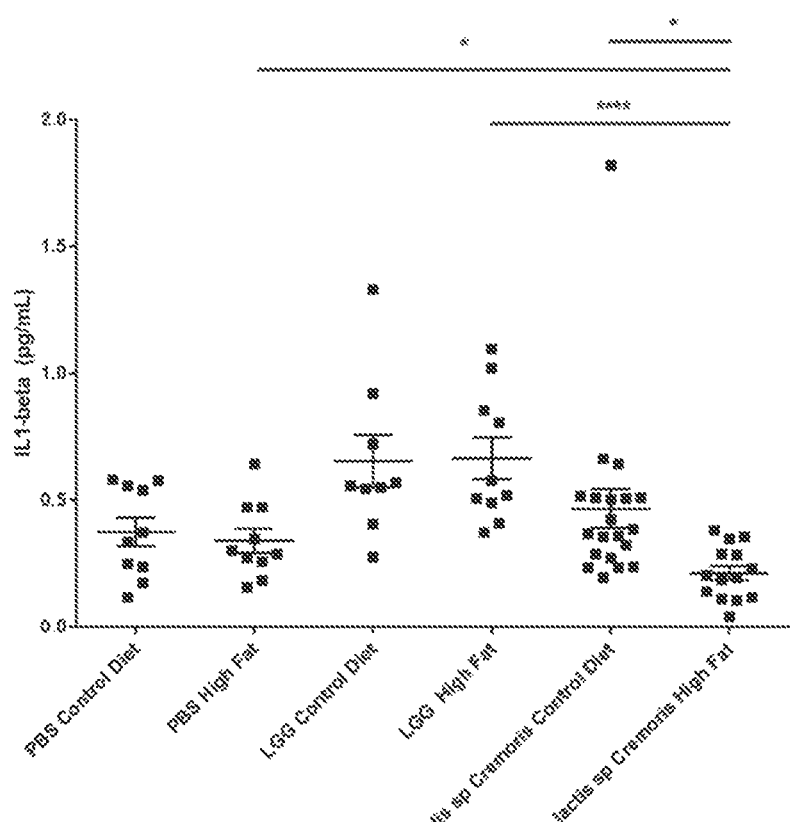

FIG. 7 shows data indicating that *Lactococcus lactis* subsp. *cremoris* ATCC® 19257 reduces the amount of IL-1β in high-fat fed mice.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

"Administering" includes any mode of administration, such as oral, subcutaneous, sublingual, transmucosal, parenteral, intravenous, intra-arterial, buccal, sublingual, topical, vaginal, rectal, ophthalmic, nasal, inhaled, and transdermal. "Administering" can also include prescribing or filling a prescription for a dosage form comprising a particular compound. "Administering" can also include providing directions to carry out a method involving a particular composition or a dosage form comprising an agent disclosed herein.

"Effective amount" means the amount of an active substance that, when administered to a subject for treating a disease, disorder, or other undesirable medical condition, is sufficient to have a beneficial effect with respect to that disease, disorder, or condition. The effective amount will vary depending on the biological identity and formulation form of the active substance, the disease or condition and its severity, and the age, weight, and other relevant characteristics of the patient to be treated.

*Lactococcus lactis* and *Lactococcus lactis* Subsp. *cremoris* ATCC® 19257

In certain embodiments, the non-pathogenic bacteria of this disclosure comprise *Lactococcus lactis*. *Lactococcus lactis* is a gram-positive bacterium species in the *Lactococcus* genus. It is used in the dairy industry in the manufacture of fermented dairy products. Based on its history in food fermentation, *Lactococcus lactis* has been generally recognized as safe (GRAS). Notably, *Lactococcus lactis* is subdivided into *Lactococcus lactis* subsp. *lactis* and *Lactococcus lactis* subsp. *cremoris*.

In certain embodiments, the specific *Lactococcus lactis* strain of this disclosure is *Lactococcus lactis* subsp. *cremoris*. *Lactococcus lactis* subsp. *cremoris* was first described by Orla-Jensen after isolation from Danish raw milk, hard cheeses, and cream samples. It can be distinguished from closely related strains of *Lactococcus lactis* subsp. *lactis* by a few phenotypic characteristics, including a lower optimal growth temperature, typically an inability to grow at pH 9.2 or in the presence of 4% NaCl, and a lack of arginine deiminase. Strains of *Lactococcus lactis* subsp. *cremoris* have also been reported to have high β-galactosidase activities and to be unable to transport large peptides into their cells. See Salama et al. Applied and Environmental Microbiology, 1993, Vol. 59, No. 11, 3941-3945. The ATCC® deposit number of *Lactococcus lactis* subsp. *cremoris* is 19257.

*Lactococcus lactis* subsp. *cremoris* ATCC® 19257 dampens inflammation and tissue damage in the intestine and exhibits cryoprotective effect against ionizing radiation. Current interventional therapies for intestinal inflammation include oral dosing of 5-aminosalicyclic acid, antibiotics, corticosteroids and immunomodulators, and subcutaneous or intravenous administration of biologics. Animal studies performed herein demonstrate that *Lactococcus lactis* subsp. *cremoris* ATCC® 19257 preserves gut tissue health in response to induced inflammation or injury. Importantly, the detected beneficial influences are a specific property of *Lactococcus lactis* subsp. *cremoris* ATCC® 19257, since other closely related strains from the same taxa did not exhibited similar influences in the same gut injury and colitis models. *Lactococcus lactis* subsp. *cremoris* ATCC® 19257 conferred significantly more efficacious influences in dampening intestinal inflammation in the gut injury and colitis models compared to *Lactobacillius rhamnosus* GG, which is a widely marketed and well studied beneficial bacterium. In addition, *Lactococcus lactis* subsp. *cremoris* ATCC® 19257 protected mice from ionizing radiation-induced mortality.

*Lactococcus lactis* subsp. *cremoris* ATCC® 19257 influences lipid metabolism. Animal experiments performed here demonstrate that *Lactococcus lactis* subsp. *cremoris* ATCC® 19257 influences lipid metabolism at the organismal level. Specifically, *Lactococcus lactis* subsp. *cremoris* ATCC® 19257 significantly decreased weight gain rates in mice fed a high-fat, high-carbohydrate Western diet whereas *Lactobacillius rhamnosus* GG did not show any pronounced effect. In addition, *Lactococcus lactis* subsp. *cremoris* ATCC® 19257 reduced liver fat accumulation and decreased serum cholesterol levels in mice fed the Western diet. It also protected against Western diet-induced liver steatosis.

Methods of Use

This disclosure relates to methods of using beneficial bacterial such as, a *Lactococcus lactis* strain, to manage, treat, or prevent obesity, fatty liver diseases, harmful ionizing radiation, metabolic syndrome, gastrointestinal diseases, and other conditions or aliments. In certain embodiments, the subject is at risk or, susceptible to, exhibiting symptoms of, or diagnosed with a disease or conditions disclosed herein. In certain embodiments, methods comprise administering an effective amount of a *Lactococcus lactis* strain to a subject in need thereof. In certain embodiments, the *Lactococcus lactis* strain is *Lactococcus lactis* subsp. *cremoris* ATCC® 19257 or a mutant thereof.

This disclosure relates to methods of using beneficial bacterial such as, a *Lactococcus lactis* strain, to treat or prevent fatty liver diseases such as hepatic steatosis, nonalcoholic fatty liver disease (NAFLD) and nonalcoholic steatohepatitis (NASH). With regard to any of the methods disclosed herein, the *Lactococcus lactis* strain is *Lactococcus lactis* subsp. *cremoris* ATCC® 19257 or a mutant thereof.

In certain embodiments, the disclosure relates to methods of treating hepatic steatosis or NAFLD comprising administering an effective amount of a beneficial bacterial such as, a *Lactococcus lactis* strain, to a subject in need thereof. In certain embodiments, the subject is at risk of, exhibiting symptoms, or diagnosed with NAFLD or metabolic syndrome.

In certain embodiments, the disclosure relates to methods of treating NASH by administering an effective amount a beneficial bacterial such as, a *Lactococcus lactis* strain, to a subject in need thereof. In certain embodiments, the subject is at risk of, exhibiting symptoms, or diagnosed with NASH. In certain embodiments, the disclosure relates to methods of preventing NASH by administering an effective amount a beneficial bacterial such as, a *Lactococcus lactis* strain, to a subject in need thereof. In certain embodiments, the subject is diagnosed with NAFLD.

In certain embodiments, a subject is at risk of NAFLD due to obesity, insulin resistance, an enlarged liver, signs of cirrhosis, or abnormal levels of liver enzymes, triglycerides and/or cholesterol. Signs of insulin resistance include darkened skin patches over your knuckles, elbows, and knees. Signs of cirrhosis include jaundice, a condition that causes your skin and whites of your eyes to turn yellow. A sign of NAFLD or NASH includes blood test showing increased levels of the liver enzymes alanine aminotransferase (ALT) and aspartate aminotransferase (AST). An enlarged liver or an abnormal amount of fat in a liver may be identified by ultrasound, computerized tomography (CT) scans, magnetic resonance imaging or combinations thereof. A liver biopsy may be used to detect liver inflammation and damage to diagnose NASH.

Metabolic syndrome is typically diagnosed in the presence of three or more of the following medical issues: large waste size, e.g., 40 inches or more, high triglycerides e.g., triglyceride level of 150 mg/dL or higher, low levels of HDL cholesterol less than 50 mg/dL, high blood pressure, e.g., 130/85 mmHg or higher, and high blood glucose (or blood sugar) levels, a fasting blood sugar level of 100 mg/dL or higher.

In another aspect, the disclosure relates to methods to promote gut health, comprising administrating non-pathogenic bacteria in an effective amount to a subject in need thereof, wherein the non-pathogenic bacteria comprise a *Lactococcus lactis* strain. In certain embodiments, the subject is at risk of, exhibiting symptoms, or diagnosed with gastrointestinal diseases, comprising colitis, enteritis, enterocolitis, celiac disease, inflammatory bowel disease, increased intestinal permeability (leaky gut syndrome), diverticular disease, colonic polyps or cancer, intestinal cancer, and irritable bowel syndrome. In certain embodiments, the subject is on a diet low in fiber. In certain embodiments, the subject is on a diet high in dairy products.

In another aspect, the disclosure relates to methods to control body weight or decrease the weight gain rate, comprising administrating non-pathogenic bacteria in an effective amount to a subject in need thereof, wherein the non-pathogenic bacteria comprise a *Lactococcus lactis* strain. In certain embodiments, the subject is on a high-fat Western diet prior to the administration of the non-pathogenic bacteria. In certain embodiments, the high-fat Western diet is characterized by high intakes of red and processed meat, butter, fried foods, high-fat dairy products, eggs, refined grains, potatoes, and high-sugar drinks. In certain embodiments, the high-fat Western diet has more than 35% of the calories derived from fat and more than 40% of the calories derived from carbohydrates, wherein more than 60% of the calories derived from carbohydrates are derived from sucrose. In certain embodiments, the subject is overweight, as characterized by a Body Mass Index (BMI) between 25 and 29.9. In certain embodiments, the subject has obesity, as characterized by a BMI of 30 or over. In certain embodiments, the subject has obesity-related conditions and complications, comprising stroke and type 2 diabetes.

In another aspect, the disclosure relates to methods to control or reduce the serum cholesterol level, comprising administrating non-pathogenic bacteria in an effective amount to a subject in need thereof, wherein the non-pathogenic bacteria comprise a *Lactococcus lactis* strain. In certain embodiments, the subject has a borderline high serum cholesterol level, 200-239 mg/dL. In certain embodiments, the subject has a high serum cholesterol level, >240 mg/dL. In certain embodiments, the subject is at risk of, exhibiting symptoms, or diagnosed with hypercholesterolemia.

In another aspect, the disclosure relates to methods to prevent or treat hepatic steatosis, comprising administrating non-pathogenic bacteria in an effective amount to a subject in need thereof, wherein the non-pathogenic bacteria comprise a *Lactococcus lactis* strain. In certain embodiments, the subject is at risk of, exhibiting symptoms of, or diagnosed with alcoholic liver disease (ALD). In certain embodiments, the subject is at risk of, exhibiting symptoms of, or diagnosed with alcoholic steatohepatitis (ASH). In certain embodiments, the subject is at risk of, exhibiting symptoms of, or diagnosed with nonalcoholic fatty liver disease (NAFLD). In certain embodiments, the subject is at risk of, exhibiting symptoms of, or diagnosed with nonalcoholic steatohepatitis (NASH). In certain embodiments, a subject is at risk of NAFLD due to obesity, insulin resistance, an enlarged liver, signs of cirrhosis, or abnormal levels of liver enzymes, triglycerides and/or cholesterol. Signs of insulin resistance include darkened skin patches over your knuckles, elbows, and knees. Signs of cirrhosis include jaundice, a condition that causes skin and whites of eyes to turn yellow. A sign of NAFLD or NASH includes blood test showing increased levels of the liver enzymes alanine aminotransferase (ALT) and aspartate aminotransferase (AST). An enlarged liver or an abnormal amount of fat in a liver may be identified by ultrasound, computerized tomography (CT) scans, magnetic resonance imaging or combinations thereof. A liver biopsy may be used to detect liver inflammation and damage to diagnose NASH.

In certain embodiments, the non-pathogenic bacteria are in the form of aqueous solution, suspension, lyophilizate, or powder. In certain embodiments, the non-pathogenic bacteria are administrated to the subject in different pharmaceutical and nutraceutical formulations, comprising beads, capsules, tablets, gels, and liquid suspensions. In certain embodiments, the non-pathogenic bacteria are administrated to the subject in the form of probiotic food and beverage products, including milk, yogurts, cheeses, creams, chocolates, meats, and other fermentation products. In certain embodiments, the *Lactococcus lactis* strain is *Lactococcus lactis* subsp. *cremoris* ATCC® 19257 or a mutant thereof. In certain embodiments, the *Lactococcus lactis* strain is *Lactococcus lactis cremoris* subsp. ATCC® 19257 or a mutant thereof. In certain embodiments, the non-pathogenic bacteria also include other beneficial bacteria species, comprising *Lactobacillus rhamnosus, Lactobacillus acidophilus, Lactobacillus plantarum, Lactobacillus casei, Lactobacillus delbrueckii, Lactobacillus brevis, Lactobacillus johnsonii, Lactobacillus fermentum, Lactobacillus reuteri, Bifidobacterium infantis, Bifidobacterium animalis, Bifidobacterium bifidum, Bifidobacterium longum, Bifidobacterium breve, Saccharomyces boulardi, Enterococcus durans, Enterococcus faecium, Streptococcus thermophilus, Pediococcus acidilactici, Leuconostoc mesenteroides, Bacillus coagulans, Bacillus subtilis*, and *Bacillus cereus*.

This disclosure relates to methods to protect against or treat symptoms caused by harmful ionizing radiation exposure, comprising administrating non-pathogenic bacteria in an effective amount to a subject in need thereof, wherein the non-pathogenic bacteria comprise a *Lactococcus lactis* strain. In certain embodiments, the harmful ionizing radiation exposure comprises X-rays, gamma rays, and particles. In certain embodiments, the radiation exposure is originated from occupational exposure, comprising healthcare facilities, research institutions, baggage-scanning facilities, nuclear reactors and support facilities, nuclear weapon production facilities, mining facilities, and other manufacturing settings. In certain embodiments, the radiation exposure is originated from non-occupational exposure, comprising medical exposure, radiation fallout from nuclear weapon tests and uses, and releases from nuclear power facilities. In certain embodiments, the medical exposure is originated from medical diagnostics and therapeutics, comprising radiology and radiation therapies. In certain embodiments, the radiation therapies comprise radiation therapies for cancer. In certain embodiments, the non-pathogenic bacteria are administrated prior to the radiation exposure. In certain embodiments, the non-pathogenic bacteria are administrated after the radiation exposure and the subject may or may not develop radiation symptoms, comprising nausea and vomiting, cough, fever, fullness of the chest, shortness of breath, severe fatigue, spontaneous bleeding, bloody diarrhea, sloughing of skin, hair loss, dry mouth, mouth ulcers, difficulty swallowing, stiffness in the joints or muscles, lymphedema, tooth decay, bladder irritation, radiation fibrosis, infections, erectile dysfunction in men, lowered sperm counts or reduced sperm activity in men, changes of menstruation in women, symptoms of menopause in women, and infertility in women.

In certain embodiments, this disclosure relates to methods of treating fibrosis or a fibrotic disease or condition in a subject in need thereof comprising administering to the subject a therapeutically effective amount of a pharmaceutical composition comprising beneficial bacterial such as, a *Lactococcus lactis* strain. In certain embodiments, the fibrosis or fibrotic disease or condition is liver fibrosis or renal fibrosis. In certain embodiments, the liver fibrosis is associated with fatty liver diseases such as, hepatic steatosis, NASH or NAFLD.

Fibrosis is the formation of excess fibrous connective tissue in an organ or tissue in a reparative or reactive process. This can be a reactive, benign, or pathological state. The deposition of connective tissue in the organ and/or tissue can obliterate the architecture and function of the underlying organ or tissue. Fibrosis is this pathological state of excess deposition of fibrous tissue, as well as the process of connective tissue deposition in healing.

Fibrosis is similar to the process of scarring, in that both involve stimulated cells laying down connective tissue, including collagen and glycosaminoglycans. Hepatocyte damage resulting from factors such as fat accumulation, viral agents, excessive alcohol consumption, hepatoxins, inevitably triggers an inflammatory immune response. The increased production of cytokines and chemokines in the liver leads to recruitment of pro-inflammatory monocytes (precursor cells) that subsequently mature into pro-inflammatory macrophages. Pro-inflammatory macrophages are pro-fibrogenic in nature and ultimately lead to the activation of hepatic stellate cells (HSCs) that are primarily responsible for the deposition of extracellular matrix (ECM).

Infiltration of various immune cell populations, resulting in inflammation, is a pathogenic feature following acute- and chronic liver injury. Chronic liver inflammation leads to continuous hepatocyte injury which can lead to fibrosis and cirrhosis. Interactions between intra-hepatic immune cells lead to increased activation and migration of Kupffer cells and HSCs. Disruption of the intestinal microbiota and its downstream effects on the gut-liver axis both play an important role in metabolic disorders such as obesity, NAFLD and NASH.

In some embodiments, the present disclosure provides for methods of treating subjects at risk of developing liver fibrosis or cirrhosis. In further embodiments, liver fibrosis is associated with emerging cirrhosis. In some embodiments, the fibrosis or cirrhosis is associated with alcohol damage.

In certain embodiments, methods disclosed herein comprise detecting a level of one or biological molecules in the subject treated for fibrosis or the fibrotic disease or condition or condition, wherein an increase or decrease in the level of one or more biological molecules compared to a predetermined standard level is predictive of the treatment efficacy of fibrosis or the fibrotic disease or condition, wherein the biological molecule is selected from the group consisting of lipopolysaccharide (LPS), LPs-binding protein (LBP), 16S rDNA, sCD14, intestinal fatty acid binding protein (I-FABP), zonulin-1, Collagen 1a1 and 3a1, TGF-beta, fibronectin-1, hs-CRP, IL-1beta, IL-6, IL-33, fibrinogen, MCP-1, MIP-1alpha and -1beta, RANTES, sCD163, TGF-beta, TNF-alpha, a biomarker of hepatocyte apoptosis such as CK-18 (caspase-cleaved and total), and a combination thereof.

In certain embodiments, the one or more biological molecules are measured in a biological sample from a subject treated for fibrosis or the fibrotic disease or condition. In certain embodiments, the biological sample is selected from blood, skin, hair follicles, saliva, oral mucous, vaginal mucous, sweat, tears, epithelial tissues, urine, semen, seminal fluid, seminal plasma, prostatic fluid, pre-ejaculatory fluid (Cowper's fluid), excreta, biopsy, ascites, cerebrospinal fluid, lymph, brain, and tissue extract sample or biopsy sample.

In certain embodiments, this disclosure relates to methods of delaying or preventing NASH comprising administering to a patient at risk of developing NASH a therapeutically effective amount of a pharmaceutical composition comprising beneficial bacterial such as, a *Lactococcus lactis* strain, wherein delay or prevention of NASH is measured by changes from baseline in inflammatory biomarkers. In certain embodiments, the level of inflammatory biomarker is increased or decreased after administration of the pharmaceutical composition compared with level of inflammatory biomarker at baseline.

In certain embodiments, this disclosure relates to methods of delaying or preventing NASH comprising administering to a patient at risk of developing NASH a therapeutically effective amount of a pharmaceutical composition comprising beneficial bacterial such as, a *Lactococcus lactis* strain, wherein delay or prevention of NASH is measured by changes from baseline measurements of fibrosis.

In certain embodiments, the measurement of fibrosis is increased or decreased after administration of the pharmaceutical composition compared with measurement of fibrosis at baseline.

In certain embodiments, the disclosure provides methods for reducing the amount of liver fat or the accumulation of liver fat in the subject comprising administering beneficial bacterial such as, a *Lactococcus lactis* strain alone or in combination with a statin. In some embodiments of the second aspect, the method is a method of treating a subject to reduce or prevent steatosis comprising administering a beneficial bacterial such as, a *Lactococcus lactis* strain alone or in combination with a statin. In some embodiments, the statin is atorvastatin, rosuvastatin, simvastatin, pravastatin, lovastatin, fluvastatin, or pitavastatin.

In certain embodiments, this disclosure relates to methods of treating fatty liver disease in the subject comprising administering a beneficial bacterial such as, a *Lactococcus lactis* strain alone or in combination with a statin. Another embodiment is a method of treating a liver disease where in the liver disease is hepatic steatosis or NAFLD. In some embodiments, the method is a method of treating a subject to prevent or reduce the rate of progression of liver disease. In some embodiments, the liver disease is NASH. In some embodiments, the liver disease is alcoholic hepatic steatosis.

In any of the embodiments, the subject may have a risk factor for developing fatty liver (steatosis) wherein the risk factor is that the subject has metabolic syndrome, type-2 diabetes, impaired glucose tolerance, obesity, dyslipidemia, hepatitis B, hepatitis C, an HIV infection, or a metabolic disorder such as Wilson's disease, a glycogen storage disorder, or galactosemia. In some embodiments, the patient has diabetes mellitus. In some embodiments, the patient has an inflammatory condition. In some embodiments, the patient has an elevated body mass index above what is normal for gender, age and height.

In certain embodiments, this disclosure relates to uses of beneficial bacterial such as, a *Lactococcus lactis* strain for improving digestive health. In certain embodiments, methods comprise administering an effective amount of a *Lactococcus lactis* strain to a subject in need thereof to manage, treat or prevent, inflammatory bowel diseases, Crohn's disease, ulcerative colitis, diarrhea, rotaviral diarrhea, antibiotic-associated diarrhea, urinary tract infections, vaginal yeast infections, irritable bowel syndrome, necrotizing enterocolitis, reduce gas, bloating, constipation, ulcers, cancer, depressed immune function, inadequate lactase digestion, infant allergies, failure-to-thrive, hyperlipidaemia, stomach cancer, and *Helicobacter pylori* infections.

Probiotic Formulations

In certain embodiments, this disclosure contemplates that beneficial bacterial such as, a *Lactococcus lactis* strain disclosed herein are in a probiotic supplement formulation, or food. In certain embodiments, this disclosure contemplates that beneficial bacterial such as, a *Lactococcus lactis* strain disclosed herein, such *Lactococcus lactis* subsp. *cremoris* ATCC® 19257 or a mutant thereof, is combination with other probiotics, such as other bacteria and yeast, such as strains of *Lactobacillus, Streptococci, Enterococci, Pediococci, Bacilli, Bifidobacterium, Lactobacillus acidophilus, Lactobacillus fermentum, Lactobacillus casei, Lactobacillus rhamnosus, Lactobacillus salivarius, Lactobacillus reuteri, Streptococcus thermophilus*, and certain yeast (*Saccharomyces boulardii* and *Saccharomyces cerevisiae*).

In certain embodiments, this disclosure contemplates that beneficial bacterial such as, a *Lactococcus lactis* strain disclosed herein is in a probiotic formulation as a powder, capsule, tablet, drops, oil suspensions, chewing gum, lozenges, stick packs and straw optionally comprising an excipient. In certain embodiments, this disclosure contemplates that beneficial bacterial such as, a *Lactococcus lactis* strain disclosed herein are in combination with vitamins, vitamin C, vitamin K, and prebiotics, carbohydrates that are not digested by the human body, inulin, fructooligosaccharides, beta-glucan, glucomannan, arabinoxylan oligosaccharides, pectin, short-chain fatty acids, butyrate, acetate and propionate.

In certain embodiments, this disclosure contemplates that beneficial bacterial such as, a *Lactococcus lactis* strain disclosed herein is in a probiotic formulation comprising an excipient such as a saccharide, polysaccharide, diluent, lubricant, colorant, binder, coating agent, sweetening agent, anti-caking agent, or suppository base such as triglycerides, polyglycolysed glycerides, polyethylene glycols (PEGs) with oil (lubercant), cocoa butter. Other contemplated excipients are microcrystalline cellulose (as binder/diluent), maltodextrin (as binder/diluent), silicon dioxide (gliding/anti-caking agent), magnesium stearate (as lubricant), hydroxy propyl methyl cellulose (as suspending/viscosity agent). In certain embodiments, the excipient is selected from a saccharide, disaccharide, sucrose, lactose, glucose, mannitol, sorbitol, polysaccharides, starch, cellulose, microcrystalline cellulose, cellulose ether, hydroxypropyl cellulose (HPC), xylitol, sorbitol, maltitol, gelatin, polyvinylpyrrolidone (PVP), polyethylene glycol (PEG), hydroxypropyl methylcellulose (HPMC), crosslinked sodium carboxymethyl cellulose, dibasic calcium phosphate, calcium carbonate, stearic acid, magnesium stearate, talc, magnesium carbonate, silica, vitamin A, vitamin E, vitamin C, retinyl palmitate, selenium, cysteine, methionine, citric acid, and sodium citrate, and combinations thereof.

In certain embodiments, beneficial bacterial such as, a *Lactococcus lactis* strain, in doses between $10^4$ and $10^{11}$ colony forming units (cfu). In certain embodiments, beneficial bacterial such as, a *Lactococcus lactis* strain, in doses between $10^5$ and $10^{10}$ colony forming units (cfu). In certain embodiments, beneficial bacterial such as, a *Lactococcus lactis* strain, in doses between $10^6$ and $10^9$ colony forming units (cfu). In certain embodiments, the doses are administered daily. In certain embodiments, oral, vaginal or rectal delivery is contemplated

EXAMPLES

*Lactococcus lactis* Subsp. *cremoris* ATCC® 19257 Confers Potent Cytoprotective Effects in the *Drosophila* Intestine in Response to Oxidative Challenge.

Figure 1:
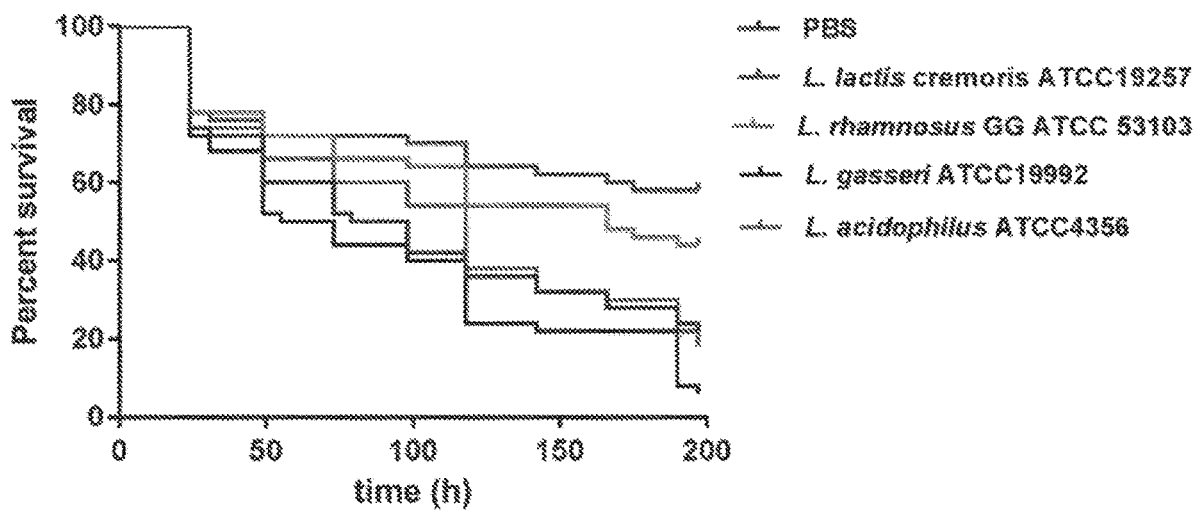
FIG. 1 shows data indicating that *Lactococcus lactis* subsp. *cremoris* ATCC® 19257 confers potent cytoprotective effects in the *Drosophila* intestine in response to oxidative challenge. Relative survival of germ-free adult *Drosophila* gnotobiotically monocolonized with the indicated lactic acid bacteria in response to Paraquat challenge was shown. Significantly enhanced survival of only flies monocolonized with *L. lactis* subsp. *cremoris* ATCC® 19257 (Log-Rank test for g-f vs. g-f+*L. lactis* subsp. *cremoris*, P<=0.0006, n=50), or monocolonized with *Lactobacillus rhamnosus* GG (Log-Rank test for g-f vs. g-f+*L. rhamnosus* GG, P<=0.0202, n=50) was observed.

The survival in response to Paraquat of 5-day-old germ-free adult *Drosophila* gnotobiotically monocolonized with candidate lactic acid bacteria was examined. Of those tested, flies gnotobiotically monocolonized with pure cultures of *Lactococcus lactis* subsp. *cremoris* ATCC® 19257 were highly protected against oxidative injury as determined by increased survival in response to Paraquat (FIG. 1). *Lactobacillus rhamnosus* GG, a well-studied beneficial bacterium, also elicited cytoprotection against Paraquat-toxicity in the fly model albeit to a milder extent compared to *L. lactis* sp. *cremoris* ATCC® 19257 (FIG. 1). Importantly, other lactic acid bacteria strains tested, namely *Lactobacillus gasseri* ATCC® 19992 and *Lactobacillus acidophilus* ATCC® 4356, did not elicit cytoprotection in this assay, showing that the capacity of bacteria to elicit beneficial influences on the host is specific and is variable even within closely related bacterial taxa.

Ingestion of *Lactococcus lactis* Subp. *cremoris* ATCC® 19257 is Cytoprotective Against Ionizing Radiation Insult in Mice.

The extent to which *Lactococcus lactis* subsp. *cremoris* elicited cytoprotection against ionizing radiation insult were examined. C57BL/6 mice were fed either vehicle control, or $1 \times 10^8$ CFU of candidate lactic acid bacteria strains once per day for 3 days. Thereafter, the experimental groups were subjected to whole body ionizing radiation at 12 Gy of γ-radiation using a γ-Cell 40 $^{137}$Cs irradiator at a dose rate of 75 rads/min, whereupon murine weights were recorded daily thereafter. Mice fed either *L. lactis* subsp. *cremoris* ATCC® 19257 or *L. rhamnosus* GG exhibited significantly enhanced preservation of body weight and survival rates compared to vehicle control (FIG. 2). Together, these data show that *L. lactis* sp. *cremoris* ATCC® 19257 elicits cytoprotection from radiation damage.

*Lactococcus lactis* Subp. *cremoris* ATCC® 19257 Protects the Murine Intestine from Dextran Sodium Sulfate (DSS)-Induced Colitis.

Dextran sodium sulfate (DSS) was used to induce gut injury and establish a colitis model to assess the efficacy of *Lactococcus lactis* subsp. *cremoris* at modulating murine intestinal inflammation. C57BL/6 mice were fed either $1 \times 10^8$ CFU *L. lactis* subsp. *cremoris* ATCC® 19257, *L. rhamnosus* GG or vehicle control daily for 14 days. After 14 days, feeding of the bacteria ceased, and 4% DSS was included in the drinking water of the experimental groups. As expected, mice fed the vehicle control responded to DSS by exhibiting considerable weight loss, the presence of blood in fecal pellets, and high Disease Activity Index (DAI) starting at 4 days following DSS ingestion (FIGS. 3A and B). Mice fed *L. rhamnosus* GG exhibited similar weight loss compared to the vehicle control, and for the most part (except for day 7), exhibited no significant difference in DAI compared to the vehicle control (FIGS. 3A and B). Strikingly, mice fed *L. lactis* subsp. *cremoris* ATCC® 19257 exhibited significant reduced weight loss and decreased DAI in response to DSS (FIGS. 3A and B). Examination of colonic tissue at 10 days following onset of DSS treatment confirmed DAI observations in live animals, where *L. lactis* subsp. *cremoris* ATCC® 19257 (but not *L. rhamnosus* GG) fed mice exhibited significantly preserved colon length, and weight to length ratio compared to the vehicle fed control (FIGS. 3C and D). Together, these data show that *L. lactis* subsp. *cremoris* ATCC® 19257 dampened outward disease symptoms and intestinal tissue damage induced by a DSS-induced gut injury and colitis model in mice.

*Lactococcus lactis* Subp. *cremoris* ATCC® 19257 Protects Against Western Diet-Induced Weight Gain, Liver Fat Accumulation, and Serum Cholesterol Level Increase.

6-week-old C57BL/6 mice were fed for 17 weeks with either a Western diet containing 40% fat (95% milk fat, 5% corn oil), 43% carbohydrate (70% sucrose, 20% maltodextrin 10, 10% corn starch), and 17% protein (Research Diets Inc. Cat. #D12079B, New Brunswick, NJ) or a control diet containing 10% fat (81% milk fat, 19% corn oil), 73% carbohydrate (18% maltodextrin 10, 82% corn starch), and 17% protein (Research Diets Inc. Cat. #D14042701). The two diets are calorie matched per gram. Mice were found to eat, on average, the same volume of food per day. Mice were supplemented twice weekly with either $2\times10^9$ CFU of *Lactobacillus rhamnosus* GG (LGG), or with $2\times10^9$ CFU *Lactococcus lactis* subsp. *cremoris* ATCC® 19257, or vehicle (PBS) as a feeding control. Supplementation of *L. lactis* subsp. *cremoris* ATCC® 19257 suppressed Western diet-induced weight gain whereas supplementation with LGG did not (FIG. 4). *L. lactis* subsp. *cremoris* ATCC® 19257 also reduced liver fat accumulation (FIGS. 5A and B), and the total serum cholesterol level (FIG. 6).

*Lactococcus lactis* Subsp. *cremoris* ATCC® 19257 has Potential Anti-Inflammatory Effects through the Reduction of Interleukin 1-beta (IL-1β) Cytokine Levels in the Serum of High-Fat Diet Fed Mice.

The IL-1β potent pro-inflammatory cytokine plays a key role in the activation of the inflammasome that functions in tissue injury and immune cell recruitment. $1\times10^8$ CFU of *Lactococcus lactis* subsp. *cremoris* ATCC® 19257, or *Lactobacillus rhamnosus* GG, or PBS vehicle control was administered by oral gavage to C57BL/6 J mice for three days per week by oral gavage. Groups of mice were fed either a high-fat diet (Bio Sery F3282, Flemington, NJ) or a control diet (Bio Sery F4031 Flemington, NJ). After 14 weeks of feeding, the animals were sacrificed and serum collected from each mouse. Analysis of the serum for IL-1β (pg/mL) was conducted using the MesoScale Discovery platform on a V-PLEX Proinflammatory Cytokine Panel 1 kit (K D). Statistical analysis was performed by Unpaired T test. *=P<0.05, ****=P<0.0001. As shown in FIG. 7, feeding of mice *L. lactis* subsp. *cremoris* ATCC® 19257 reduced the amount of IL-1β in high-fat diet fed mice.

What is claimed is:

1. A method of treating hepatic steatosis in a patient diagnosed with or exhibiting symptoms of nonalcoholic fatty liver disease (NAFLD), the method comprising administering to the patient effective doses of the non-pathogenic bacteria *Lactococcus lactis cremoris* ATCC® 19257.

2. The method of claim 1, wherein the non-pathogenic bacteria *Lactococcus lactis cremoris* ATCC® 19257 are administered to the patient in a formulation comprising beads, capsules, tablets, gels, and liquid suspensions.

3. The method of claim 1, wherein the non-pathogenic bacteria are administered to the patient in the form of a probiotic food, a fermented food, meat, chocolate, cheese, cream, or a beverage product selected from milk, yoghurt, and kombucha.

4. The method of claim 1, wherein the effective doses of the non-pathogenic bacteria are between $10^4$ and $10^{11}$ colony forming units.

5. The method of claim 1, wherein the administering is by oral mode of administering.

* * * * *